US006380409B1

(12) United States Patent
Saebo et al.

(10) Patent No.: US 6,380,409 B1
(45) Date of Patent: Apr. 30, 2002

(54) METHODS FOR PREPARING CLA ISOMERS

(75) Inventors: Asgeir Saebo, Eidsnes; Per Christian Saebo, Volda, both of (NO)

(73) Assignee: Conlin Co., Inc., Detroit Lakes, MN (US)

(*) Notice: Subject to any disclaimer, the term of this patent is extended or adjusted under 35 U.S.C. 154(b) by 0 days.

(21) Appl. No.: 09/563,072

(22) Filed: Apr. 24, 2000

(51) Int. Cl.$^7$ ................................................. C11C 3/14
(52) U.S. Cl. ........................................ 554/126; 554/125
(58) Field of Search ................................. 554/125, 126

(56) References Cited

U.S. PATENT DOCUMENTS

| | | | | |
|---|---|---|---|---|
| 2,242,230 A | * | 5/1941 | Burr | 260/398 |
| 2,350,583 A | * | 6/1944 | Bradley | 260/195.6 |
| 3,162,658 A | * | 12/1964 | Baltes et al. | 260/405.6 |
| 3,729,379 A | * | 4/1973 | Emken | 195/30 |
| 4,164,505 A | * | 8/1979 | Krajca | 260/405.6 |
| 4,381,264 A | * | 4/1983 | Struve | 260/405.6 |
| 5,017,614 A | * | 5/1991 | Pariza et al. | 514/558 |
| 5,070,104 A | * | 12/1991 | Pariza et al. | 514/549 |
| 5,208,356 A | * | 5/1993 | Pariza et al. | 554/79 |
| 5,288,619 A | * | 2/1994 | Brown et al. | 435/134 |
| 5,430,066 A | * | 7/1995 | Cook et al. | 514/558 |
| 5,468,887 A | * | 11/1995 | Gupta | 554/169 |
| 5,554,646 A | * | 9/1996 | Cook et al. | 514/560 |
| 5,585,400 A | * | 12/1996 | Cook et al. | 514/560 |
| 5,674,901 A | * | 10/1997 | Cook et al. | 246/452 |
| 5,725,873 A | * | 3/1998 | Cook et al. | 424/442 |
| 5,760,082 A | * | 6/1998 | Cook et al. | 514/560 |
| 5,760,083 A | * | 6/1998 | Cook et al. | 514/560 |
| 5,804,210 A | * | 9/1998 | Cook et al. | 424/440 |
| 5,814,663 A | * | 9/1998 | Cook et al. | 514/560 |
| 5,827,885 A | * | 10/1998 | Cook et al. | 514/558 |
| 5,851,572 A | * | 12/1998 | Cook et al. | 426/2 |
| 5,855,917 A | * | 1/1999 | Cook et al. | 424/502 |
| 5,856,149 A | * | 1/1999 | Pariza et al. | 435/134 |
| 5,885,594 A | * | 3/1999 | Nilsen et al. | 424/401 |
| 5,986,116 A | * | 11/1999 | Iwata et al. | 554/126 |
| 6,015,833 A | * | 1/2000 | Saebo et al. | 514/558 |

FOREIGN PATENT DOCUMENTS

| | | |
|---|---|---|
| EP | 779033 A1 | 6/1997 |
| GB | 558881 | 9/1930 |
| WO | WO 96/34855 | 11/1996 |
| WO | WO 96/38137 | 12/1996 |
| WO | WO 97/18320 | 5/1997 |
| WO | WO 97/37546 | 10/1997 |
| WO | WO 97/46118 | 12/1997 |
| WO | WO 97/46230 | 12/1997 |
| WO | WO 98/05318 | 2/1998 |
| WO | WO 98/05319 | 2/1998 |
| WO | WO 98/49129 | 11/1998 |

OTHER PUBLICATIONS

Cowan, "Isomerization and Trans–Esterifiation," *JAOCS* 72:492–99 (1950).
Christie et al., "Isomers in Commercial Samples of Conjugated Linoleic Acid," *JAOCS* 74 (11):1231 (1997).
Kepler et al., *J. Biol. Chem.* 241:1350–54 (1966).
W. Parodi, *J. Nutr.* 127(6):1055–60 (1997).
Belury, "Conjugated Dienoic Linoleate: A Polyunsaturated Fatty Acid with Unique Chemoprotective Properties,"*Nut. Rev.* 53(4):83–9 (1995).
Ha et al., *Cancer Res.*, 50:1097 (1991).
Birt et al., *Cancer Res.*, 52:2035–s (1992).
Ip, *Am. J. Clin. Nutr.* 66(6):1523s (1997).
Sehat et al., *Lipids* 33(2):217–21 (1998).
Jie, et al., "High–Resolution Nuclear Magnetic Resonance Spectroscopy—Amplification to Fatty Acids and Triacylglycerols," *Lipids* 32 (10): 1019–34 (1997).
Scholfield and Koritalia, "A Simple Method for Preparation of Methyl trans–10,cis–12 Octadecadienoate," *JOACS* 47(8):303 (1970).
Ron Udell, Information About Conjugated Linoleic Acid, published by Soft Gel Technologies Incorporated (1998).
Sugano et al., "Conjugated Linoleic Acid Modulates Tissue Levels of Chemical Mediators and Immunoglobulins in Rats," *Lipids*, 33(5):521–27 (1998).
Haraldsson et al., *Acta Chem Scanned* 45:723 (1991).
Chin et al., *J. Nutrition* 124:694 (1994).
Matreya Catalog, 1997, pp. 33–34.
Selin CLA Product Literature, 1/97.
Hudtwalcker & Co. AS Technical Data Sheet, exact publication date unknown (1998).
Lipid Technology Newsletter, Peter J. Barnes, Ed., vol. 4, No. 5, pp. 85–86 (Oct., 1998).
Natural Lipids Ltd. AS Technical Data Sheet, Jan. 20, 1997.
Theil et al., "Conjugated Linoleic Acid Improves Performance and Body Composition in Swine," Iowa State University,Midwest Animal Sciences Meeting, Abstract 127:61 (1998).
Quinn et al., "A Comparison of Modified Tall Oil and Conjugated Linoleic Acid on Growing–Finishing Pig Growth Performance and Carcass Characteristics," Kansas State University and Lonza, Inc., Midwest Animal Sciences Meeting, Abstracat 128:61 (1998).
Dugan et al., "The Effect of Conjugated Linoleic Acid on Fat to Lean Repartitioning and Feed Conversion in Pigs," *Canadian Journal of Animal Science* 77:723–725 (1997).

(List continued on next page.)

Primary Examiner—Deborah D. Carr
(74) *Attorney, Agent, or Firm*—Medlen & Carroll, LLP

(57) ABSTRACT

Novel compositions containing conjugated linoleic acid isomers can be used for controls in gas chromatography and for animal feeding studies. Purified isomers of conjugated linoleic acid can be treated to produce a preparation containing two isomers of CLA. The preparation can be used as is or further processed to separate the two isomers. The isomers can be used in their free fatty acid form or converted to alkylesters or triglycerides. Furthermore, the isomers are useful as supplements for food products or feed.

33 Claims, No Drawings

OTHER PUBLICATIONS

Shantha et al., "Conjugated Linoleic Acid Concentrations in Processed Cheese Containing Hydrogen Donors, Iron and Dairy—Based Additives," *Food Chemistry* 47:257–261 (1993).

Bradley et al., "Alkali–Induced Isomerization of Drying Oils and Fatty Acids," *Ind. Eng. Chem.* 34(2):237–242 (1942).

Jie et al., "Synthesis and Nuclear Magnetic Resonance Properties of All Geometrical Isomers of Conjugated Linoleic Acids," *Lipids* 32(10):1041–1044 (1997).

Arcos et al., "Rapid Enzymatic Production of acylglycerols from conjugated linoleic acid and glyerol in the solvent–free system," *Biotechnology Letters* 20:617 (1998).

Holman et al., "Unusual Isomeric Polyunsaturated Fatty Acids in Liver Phospholipids of Rats Fed Hydrogenated Oil," *PNAS* 88:4830–34 (1991).

Radlove et al., "Catalytic Isomerization of Vegetable Oils," *Ind. Eng. Chem.* 38(10):997–1002 (1946).

Sebedio et al., "Linoleic Acid Isomers in Heat Treated Sunflower Oils," *JAOCS* 65(3):362–366 (1988).

Sebedio et al., "Metabolites of Conjugated Isomers of Linoleic Acid (CLA) in the Rat,"*Biochem. Biophys. Acta* 1345:5–10 (1997).

Chin et al., "Dietary Sources of Conjugated Dienoic Isomers of Linoleic Acids, a Newly Recognized Class of Anticarcinogens," *J. Food. Comp. Anal.* 5:185–197 (1992).

Park et al., "Effect of Conjugated Linoleic Acid on Body Composition in Mice," *Lipids* 32(8):853–58 (1997).

Berdeau et al., "A Simply Method of Preparation of Methyl trans–10, cis–12–and cis –9, trans–11 –Octadecadienoates from Methyl Linoleate," *JAOCS* 75:1749–1755 (1998).

Mossoba et al, Impace of novel methodologies on the analysis of conjugated linoleic acid (CLA). Implications of CLA feeding studies Abs and citation. An 1999:50498 Caplus, 1999.*

* cited by examiner

METHODS FOR PREPARING CLA ISOMERS

FIELD OF THE INVENTION

The present invention relates to lipid biochemistry, and in particular to the preparation of various isomers of conjugated linoleic acid.

BACKGROUND OF THE INVENTION

In 1978, researchers at the University of Wisconsin discovered the identity of a substance contained in cooked beef that appeared to inhibit mutagenesis. The substance was found to be a mixture of positional isomers of linoleic acid (C18:2) having conjugated double bonds. The c9,t11 and t10,c12 isomers are present in greatest abundance, but it is uncertain which isomers are responsible for the biological activity observed. It has been noted from labelled uptake studies that the 9,11 isomer appears to be somewhat preferentially taken up and incorporated into the phospholipid fraction of animal tissues, and to a lesser extent the 10,12 isomer (Ha, et al., Cancer Res., 50: 1097 [1990]).

The biological activity associated with conjugated linoleic acids (termed CLA) is diverse and complex. At present, very little is known about the mechanisms of action, although several preclinical and clinical studies in progress are likely to shed new light on the physiological and biochemical modes of action. The anticarcinogenic properties of CLA have been well documented. Administration of CLA inhibits rat mammary tumorigenesis, as demonstrated by Birt, et al., Cancer Res., 52: 2035s [1992]. Ha, et al., supra, reported similar results in a mouse forestomach neoplasia model. CLA has also been identified as a strong cytotoxic agent against target human melanoma, colorectal and breast cancer cells in vitro.

Although the mechanisms of CLA action are still obscure, there is evidence that some component(s) of the immune system may be involved, at least in vivo. U.S. Pat. No. 5,585,400 (Cook, et al., incorporated herein by reference), discloses a method for attenuating allergic reactions in animals mediated by type I or IgE hypersensitivity by administering a diet containing CLA. CLA in concentrations of about 0.1 to 1.0 percent was also shown to be an effective adjuvant in preserving white blood cells. U.S. Pat. No. 5,674,901 (Cook, et al., incorporated herein by reference), disclosed that oral or parenteral administration of CLA in either free acid or salt form resulted in elevation in CD-4 and CD-8 lymphocyte subpopulations associated with cell-mediated immunity. Adverse effects arising from pretreatment with exogenous tumor necrosis factor could be alleviated indirectly by elevation or maintenance of levels of CD-4 and CD-8 cells in animals to which CLA was administered. Finally, U.S. Pat. No. 5,430,066 (Cook, et al., incorporated herein by reference), describes the effect of CLA in preventing weight loss and anorexia by immune stimulation.

Apart from potential therapeutic and pharmacologic applications of CLA as set forth above, there has been much excitement regarding the use of CLA as a dietary supplement. CLA has been found to exert a profound generalized effect on body composition, in particular redirecting the partitioning of fat and lean tissue mass. U.S. Pat. No. 5,554,646 (Cook, et al., incorporated herein by reference), discloses a method utilizing CLA as a dietary supplement in which pigs, mice, and humans were fed diets containing 0.5 percent CLA. In each species, a significant drop in fat content was observed with a concomitant increase in protein mass. It is interesting that in these animals, increasing the fatty acid content of the diet by addition of CLA resulted in no increase in body weight, but was associated with a redistribution of fat and lean within the body. Another dietary phenomenon of interest is the effect of CLA supplementation on feed conversion. U.S. Pat. No. 5,428,072 (Cook, et al., incorporated herein by reference), provided data showing that incorporation of CLA into animal feed (birds and mammals) increased the efficiency of feed conversion leading to greater weight gain in the CLA supplemented birds and mammals. The potential beneficial effects of CLA supplementation for food animal growers is apparent.

Another important source of interest in CLA, and one which underscores its early commercial potential, is that it is naturally occurring in foods and feeds consumed by humans and animals alike. In particular, CLA is abundant in products from ruminants. For example, several studies have been conducted in which CLA has been surveyed in various dairy products. Aneja, et al., (J. Dairy Sci., 43: 231 [1990]) observed that processing of milk into yogurt resulted in a concentration of CLA. (Shanta, et al., Food Chem., 47: 257 [1993]) showed that a combined increase in processing temperature and addition of whey increased CLA concentration during preparation of processed cheese. In a separate study, Shanta, et al., J. Food Sci., (60: 695 [1995]) reported that while processing and storage conditions did not appreciably reduce CLA concentrations, they did not observe any increases. In fact, several studies have indicated that seasonal or interanimal variation can account for as much as three fold differences in CLA content of cows milk (See e.g., Parodi, et al., J. Dairy Sci., 60: 1550 [1977]). Also, dietary factors have been implicated in CLA content variation (Chin, et al., J. Food Comp. Anal., 5: 185 [1992]). Because of this variation in CLA content in natural sources, ingestion of prescribed amounts of various foods will not guarantee that the individual or animal will receive the optimum doses to ensure achieving the desired nutritive effect.

In the development of a defined commercial source of CLA for both therapeutic and nutritional applications, a process for generating large amounts of defined material is needed. The problem with most CLA products made by conventional approaches is their heterogeneity, and substantial variation in isoform from batch to batch. A recent publication documents this variation and indicates the need for producers of CLA to appreciate the complex nature of their products (See Christie et al., JAOCS, 74(11): 1231 [1997]).

Considerable attention has also been given to the fact that the ingestion of large amounts of hydrogenated oils and shortenings, instead of animal tallow, results in diets high in trans-fatty acid content. For example, Holman, et al., (Proc. Nat'l. Acad. Sci., 88:4830 [1991]) showed that rats fed hydrogenated oils gave rise to an accumulation in rat liver of unusual polyunsaturated fatty acid isomers, which appeared to interfere with the normal metabolism of naturally occurring polyunsaturated fatty acids. Therefore, there exists a strong need for chemical and biological analysis of the various isomers of CLA.

SUMMARY OF THE INVENTION

The present invention relates to lipid biochemistry, and in particular to the preparation of various isomers of conjugated linoleic (octadecadienoic) acid. The present invention is not limited to the production of any particular octadecadienoic acid isomer. Indeed, a variety isomers may be prepared including, but not limited to, c9,t11 octadecadienoic acid, t8,c10 octadecadienoic acid, t10,c12 octadecadienoic acid, c11,t13 octadecadienoic acid, c7,t9 octadecadienoic acid, t6,c8 octadecadienoic acid, t11,c13 octadecadienoic acid, c12,t14 octadecadienoic acid, c6,t8 octadecadienoic acid, t5,c6 octadecadienoic acid, c5,t7 octadecadienoic acid, t4,c6 octadecadienoic acid, t3,c5 octadecadienoic acid, t12,c14 octadecadienoic acid, c13,t15 octadecadienoic acid, and 14,t16 octadecadienoic acid. The isomers can be provided as free fatty acids, alkylesters, or triglycerides.

In other embodiments, the present invention provides a composition comprising isomers of conjugated linoleic acid, wherein the composition comprises or consists essentially of at least 25% of a first isomer of octadecadienoic acid and at least 25% of a sister isomer of said first isomer. The present invention is not limited to any one pair of sister isomers. Indeed, a variety of sister isomer pairs are contemplated, including, but not limited to, c9,t11 octadecadienoic acid and t8,c10 octadecadienoic acid, t10,c12 octadecadienoic acid and c11,t13 octadecadienoic acid, c7,t9 octadecadienoic acid and t6,c8 octadecadienoic acid, t11,c13 octadecadienoic acid and c12,t14 octadecadienoic acid, c6,t8 octadecadienoic acid and t5,c6 octadecadienoic acid, c5,t7 octadecadienoic acid and t4,c6 octadecadienoic acid, c4,t6 octadecadienoic acid and t3,c5 octadecadienoic acid, t12, c14 octadecadienoic acid and c13,t15 octadecadienoic acid, and t13,c15 octadecadienoic acid and c14,t16 octadecadienoic acid. The isomers can be provided as free fatty acids, alkylesters, or triglycerides.

In still other embodiments, the present invention provides methods for preparing pairs of octadecadienoic acid isomers and individual octadecadienoic acid isomers comprising: a) providing a first partially purified octadecadienoic acid isomer: and b) treating the first octadecadienoic isomer under conditions such that the conjugated bond system migrates, thereby forming a mixture containing at least first and second isomers of octadecadienoic acid. In still further embodiments, the methods further comprise step c) separating the at least first and second isomers of octadecadienoic acid to provide a second purified octadecadienoic acid isomer. In other embodiments of the present invention, the conditions comprise heating the partially purified octadecadienoic acid isomer. In still further embodiments, the separating step is accomplished by gas liquid chromatography. In some embodiments, the first partially purified octadecadienoic acid isomer is one of c9,t11 and t8,c10 octadecadienoic acids and the second octadecadienoic acid isomer is the other of t8,c10 and c9,t11 octadecadienoic acids. In some embodiments, the first partially purified octadecadienoic acid isomer is one of t10,c12 and c11,t13 octadecadienoic acids and the second octadecadienoic acid isomer is the other of t10,c12 and c11,t13 octadecadienoic acids. In some embodiments, the first partially purified octadecadienoic acid isomer is one of c7,t9 and t6,c8 octadecadienoic acids and the second octadecadienoic acid isomer the other of c7,t9 and t6,c8 octadecadienoic acids. In some embodiments, the first partially purified octadecadienoic acid isomer is one of t11,c13 and c12,t14 octadecadienoic acids and the second octadecadienoic acid isomer is the other of t11,c13 and c12,t14 octadecadienoic acids. In some embodiments, the first partially purified octadecadienoic acid isomer is one of c6,t8 and t5,c6 octadecadienoic acids and the second octadecadienoic acid isomer is the other of c6,t8 and t5,c6 octadecadienoic acids. In other embodiments, the first partially purified octadecadienoic acid isomer is one of c5,t7 and t4,c6 octadecadienoic acids and the second octadecadienoic acid isomer is the other of c5,t7 and t4,c6 octadecadienoic acids. in some embodiments, the first partially purified octadecadienoic acid isomer is one of t3,c5 and c4,t6 octadecadienoic acids and the second octadecadienoic acid isomer is the other of c4,t6 and t3,c5 octadecadienoic acids. In some embodiments, the first partially purified octadecadienoic acid isomer is one of t12,c14 and c13,t15 octadecadienoic acids and the second partially purified octadecadienoic acid isomer is the other of t12,c14 and c13,t15 octadecadienoic acids. In other embodiments, the first partially purified octadecadienoic acid isomer is one of c14,t16 and t13,c15 octadecadienoic acids and the second octadecadienoic acid isomer is the other of said c14,t16 and t13,c15 octadecadienoic acids.

In still further embodiments, the present invention provides compositions produced by the methods described above. In some embodiments, the second isomer is present in a concentration greater than 30% of the first isomer. In other embodiments, the second isomer is present in a concentration greater than 40% of the first isomer. In still further embodiments, the second isomer is present in a concentration between 20% and 80% of the first isomer.

DEFINITIONS

As used herein, "conjugated linoleic acid" or "CLA" refers to any conjugated linoleic acid or octadecadienoic free fatty acid. It is intended that this term encompass and indicate all positional and geometric isomers of linoleic acid with two conjugated carbon—carbon double bonds any place in the molecule. CLA differs from ordinary linoleic acid in that ordinary linoleic acid has double bonds at carbon atoms 9 and 12. Examples of CLA include cis- and trans isomers ("E/Z isomers") of the following positional isomers: 2,4-octadecadienoic acid, 4,6-octadecadienoic acid, 6,8-octadecadienoic acid, 7,9-octadecadienoic acid, 8,10-octadecadienoic acid, 9,11-octadecadienoic acid and 10,12 octadecadienoic acid, 11, 13 octadecadienoic acid. As used herein, "CLA" encompasses a single isomer, a selected mixture of two or more isomers, and a non-selected mixture of isomers obtained from natural sources, as well as synthetic and semisynthetic CLA.

As used herein, the term "isomerized conjugated linoleic acid" refers to CLA synthesized by chemical methods (e.g., aqueous alkali isomerization, non-aqueous alkali isomerization, or alkali alcoholate isomerization).

As used herein, the term "conjugated linoleic acid moiety" refers to any compound or plurality of compounds containing conjugated linoleic acids or derivatives. Examples include, but are not limited to fatty acids, alkyl esters, and triglycerides of conjugated linoleic acid.

As used herein, it is intended that "triglycerides" of CLA contain CLA at any or all of three positions (e.g., SN-1, SN-2, or SN-3 positions) on the triglyceride backbone. Accordingly, a triglyceride containing CLA may contain any of the positional and geometric isomers of CLA.

As used herein, it is intended that "esters" of CLA include any and all positional and geometric isomers of CLA bound through an ester linkage to an alcohol or any other chemical group, including, but not limited to physiologically acceptable, naturally occurring alcohols (e.g., methanol, ethanol, or propanol). Therefore, an ester of CLA or esterified CLA may contain any of the positional and geometric isomers of CLA.

It is intended that "non-naturally occurring isomers" of CLA include, but are not limited to c11,t13; t11,c13; t11,t13; c11,c13; c8,t10; t8,c10, t8,t10; c8,c10; and trans—trans isomers of octadecadienoic acid. However, this definition does not include t10,c12 and c9,t11 isomers of octadecadienoic acid. "Non-naturally occurring isomers" may also be referred to as "minor isomers" of CLA, as these isomers are generally produced in low amounts when CLA is synthesized by alkali isomerization.

As used herein, "low impurity" CLA refers to CLA compositions, including free fatty acids, alkylesters, and triglycerides, which contain less than 1% total 8,10 octadecadienoic acids, 11,13 octadecadienoic acids, or trans— trans octadecadienoic acids.

As used herein, "c" encompasses a chemical bond in the cis orientation, and "t" refers to a chemical bond in the trans orientation. If a positional isomer of CLA is designated without a "c" or a "t", then that designation includes all four possible isomers. For example, 10,12 octadecadienoic acid encompasses c10,t12; t10,c12; t10,t12; and c10,c12 octadecadienoic acid, while t10,c12 octadecadienoic acid or CLA refers to just the single isomer.

As used herein, the term "oil" refers to a free flowing liquid containing long chain fatty acids (e.g., CLA), triglycerides, or other long chain hydrocarbon groups. The long chain fatty acids, include, but are not limited to the various isomers of CLA.

As used herein, the term "physiologically acceptable carrier" refers to any carrier or excipient commonly used with oily pharmaceuticals. Such carriers or excipients include, but are not limited to, oils, starches, and sugars (e.g., sucrose and lactose).

As used herein, the term "oral delivery vehicle" refers to any means of delivering a pharmaceutical orally, including, but not limited to, capsules, pills, tablets and syrups.

As used herein, the term "food product" refers to any food or feed suitable for consumption by humans, non-ruminant animals, or ruminant animals. The "food product" may be a prepared and packaged food (e.g., mayonnaise, salad dressing, bread, or cheese food) or an animal feed (e.g., extruded and pelleted animal feed or coarse mixed feed). "Prepared food product" means any pre-packaged food approved for human or animal consumption.

As used herein, the term "foodstuff" refers to any substance fit for human or animal consumption.

As used herein, the term "volatile organic compound" refers to any carbon-containing compound which exists partially or completely in a gaseous state at a given temperature. Volatile organic compounds may be formed from the oxidation of an organic compound (e.g., CLA). Volatile organic compounds include, but are not limited to pentane, hexane, heptane, 2-butenal, ethanol, 3-methyl butanal, 4-methyl pentanone, hexanal, heptanal, 2-pentyl furan, and octanal.

As used herein, the term "metal oxidant chelator" refers to any antioxidant that chelates metals. Examples include, but are not limited to lecithin and citric acid esters.

As used herein, the term "partially purify" means any process that removes some of a contaminant from the component of interest, such as removing unwanted isomers from a conjugated linoleic acid preparation. The percent of a purified component is thereby increased in the sample (i.e., the component of interest is concentrated).

As used herein, the term "sister isomers" refers to pairs of conjugated linoleic acid isomers that can be interconverted by some treatment (e.g., heating). Examples of sister isomers are provided in Table 1, infra.

As used herein, the term "conjugated bond system" refers to the following arrangement of unsaturated double bonds in a carbohydrate chain: —C=C—C=C— (i.e., two double bonds separated by a single bond).

As used herein, the term "migrate," when used in reference to a conjugated bond system in a carbohydrate chains refers to the rearrangement of unsaturated carbon—carbon double bonds within the carbohydrate chain so that the double bonds move up or down the chain.

DETAILED DESCRIPTION OF THE INVENTION

The present invention relates to lipid biochemistry, and in particular to the preparation of various isomers of conjugated linoleic acid. The rearrangement of the double bonds of linoleic acid to conjugated positions has been shown to occur during treatment with catalysts such as nickel or alkali at high temperatures, and during auto oxidation. Theoretically, eight possible geometric isomers of 9,11 and 10,12 octadecadienoic acid (c9,c11; c9,t11; t9,c11; t9,t11; c10,c12; c10,t12; t10,c12 and t10,t12) would form from the isomerization of c9,c12-octadecadienoic acid. A general mechanism for the isomerization of linoleic acid was described by J. C. Cowan (JAOCS 72:492–99 [1950]). It is believed that the double bond is polarized by the result of a collision with an activating catalyst. The polarized carbon atom and its adjoining carbon are then free to rotate and the forces are such as to make the deficient carbon atom essentially planar. When the system then moves to relieve these forces set up as a result of the collision, both cis and trans isomers are formed. The formation of certain isomers of CLA is thermodynamically favored. This is due to the co-planar characteristics of the five carbon atoms around the conjugated double bond and a spatial conflict of the resonance radical. The relatively higher distribution of 9,11 and 10,12 isomers apparently results from the further stabilization of the c9,t11 or t10,c12 geometric isomers.

Advances in gas chromatography have enabled researchers to precisely determine the isomer composition of samples of CLA. These studies demonstrate that many more than 8 isomers are actually formed during conjugation. In Christie et al., (JAOCS 74 (11):1231 [1997]), it was reported that the isomer distribution of a commercial sample of CLA was as follows: 8,10 (14%); 9,11 (30%); 10,12 (31%), and 11,13 (24%). In another study by Christie et al. in (Lipids 33(2):217–21 [1998]), the following CLA isomer composition of a commercial CLA preparation was reported: t11,t13 (0.74%); t10,t12 (1.23%); t9,t11 (1.18%); t8,t10 (0.46%); c11,t13 and t11,c13 (21.7%) c10,t12 and t10,c12 (29.0%); c9,t11 and t9,c11 (29.5%); c8,t10 and t8,c10 (12.3%); c11, c13 (0.96%); c10,c12 (0.88%); c9,c11 (0.88%); and c8,c10 (0.20%). As can be seen from these studies, even though the formation of certain isomers are favored, other isomers of CLA can contribute greatly to the composition of alkali isomerized CLA preparations.

A. Migration of Conjugated Double Bonds

The present invention provides methods for producing compositions enriched for different isomers of CLA. In some embodiments of the invention, a partially purified or concentrated isomer of CLA is treated under conditions that cause migration of the double bond system. In preferred embodiments, the conditions comprise heating at least one isomer to about 200–240° C., preferably to about 220° C. In other embodiments, the conditions further comprise reacting the partially purified or concentrated isomer or isomers under nitrogen in a sealed container. Referring to Table 1, the preparations of isomers in column 1 can be used to produce preparations containing a substantial amount of the corresponding isomer in column 2. After the initial conversion reaction, the preparation will contain both the starting isomer and the "sister" isomer. Likewise, the preparations of isomers in column 2 can be used to produce substantial amounts of the corresponding isomer in column 1. The preparations containing both isomers may be further treated to purify the sister isomer (e.g., by gas chromatography). As will be understood by those skilled in the art, it is possible to start with more than one partially purified isomer, thereby producing a preparation containing four, six, eight or more isomers. In further embodiments, a purified preparation of the sister isomer may be prepared by methods known in the art (i.e., gas-liquid chromatography) from the treated preparation containing the initial isomer and its sister isomer.

TABLE 1

| Column 1 | Column 2 |
|---|---|
| c9,t11 | t8,c10 |
| t10,c12 | c11,t13 |
| c7,t9 | t6,c8 |
| t11,c13 | c12,t14 |
| c6,t8 | t5,c6 |
| c5,t7 | t4,c6 |
| c4,t6 | t3,c5 |
| t12,c14 | c13,t15 |
| t13,c15 | c14,t16 |

As demonstrated in the Examples, treatment of purified t10,c12 octadecadienoic acid resulted in the production of c11,t13 octadecadienoic acid. Likewise, concentrated or partially purified c11,t13 octadecadienoic acid can be used to produce t10,c12 octadecadienoic acid. After the partially purified isomer is treated to produce a sister isomer, the resulting preparation preferably comprises about greater than 20% of the sister isomer as compared to the initial partially purified isomer. In other embodiments, the resulting preparation comprises about greater than 40% of the sister isomer as compared to the initial partially purified isomer. In still further embodiments, the resulting preparation comprises between about 20% and 80% of the sister isomer as compared to the initial partially purified isomer. In still other embodiments, the resulting preparation comprises or consists essentially of greater than about 20% of the sister isomer on a weight/weight basis (e.g., the preparation contains about 20 grams of the sister isomer and about 80 grams of the initial partially purified isomer). In further embodiments, the resulting preparation comprises greater than about 40% of the sister isomer on a weight/weight basis. In still further embodiments, the preparation comprises between about 20% and 80% of the sister isomer on a weight/weight basis.

B. Uses of Purified Isomer and Sister Isomer Pairs

The purified isomers and sister isomer pairs described above have many uses. In some embodiments of the present invention, the purified isomers or sister isomer pairs find use as standards in gas chromatography and liquid chromatography. Purified or enriched sources of these isomers can be used as standards for the analysis of commercial CLA products which may have contained heretofore unidentified peaks representing unidentified isomers.

In other embodiments of the present invention, the preparation containing the purified isomers or sister isomer pairs are used in animal feeding studies and as nutritional supplements. It is contemplated that the purified isomers and sister isomer pairs can be used as controls in animal feeding studies so that the biological effects (e.g., partitioning within organs and cells, effects on lipid biosynthesis, and metabolism) of the isomers can be studied. The isomers may be provided as free fatty acids, alkylesters (e.g., methyl or ethyl esters of CLA), triglycerides, or combinations thereof. In some preferred embodiments, the isomers are provided orally. In other embodiments, the isomers may be formulated with suitable carriers such as starch, sucrose or lactose in tablets, pills, dragees capsules, solutions, liquids, slurries, suspensions and emulsions. Preferably, the isomer formulations contain antioxidants, including, but not limited to Controx (Grunau (Henkel), Illertissen, Del.), Covi-OX (Grunau (Henkel), Illertissen, Del.), lecithin, and oil soluble forms of vitamin C. The isomers may be provided in aqueous solution, oily solution, or in any of the other forms discussed above. The tablet or capsule of the present invention may be coated with an enteric coating which dissolves at a pH of about 6.0 to 7.0. A suitable enteric coating which dissolves in the small intestine but not in the stomach is cellulose acetate phthalate. In some embodiments, the isomers are provided as soft gelatin capsules. The CLA may also be provided by any of a number of other routes, including, but not limited to, intravenous, intramuscular, intra-arterial, intramedullary, intrathecal, intraventricular, transdermal, subcutaneous, intraperitoneal, intranasal, enteral, topical, sublingual or rectal means. Further details on techniques for formulation for and administration and administration may be found in the latest edition of *Remington's Pharmaceutical Sciences* (Maack Publishing Co., Easton, Pa.).

An effective amount of isomers may also be provided as a supplement in various food products, including animal feeds and nutritional drinks. For the purposes of this application. "food products containing CLA isomers" refers to any natural, processed, diet or non-diet food product to which exogenous CLA isomers have been added. Likewise, "feed products containing CLA" refers to any animal feed to which exogenous CLA isomers have been added. The CLA may be added in the form of free fatty acids, esters of conjugated linoleic acid, or as an oil containing partial or whole triglycerides of CLA. Therefore, CLA may be directly incorporated into various food products, including, but not limited to diet drinks, diet bars, supplements, prepared frozen meals, candy, snack products (e.g., chips), prepared meat products, milk, cheese, yogurt and any other fat or oil containing foods.

In further embodiments of the present invention, the isomer preparations can be further purified (e.g., by molecular distillation or adsorption) to remove volatile organic compounds. Therefore, it is contemplated in some embodiments of the present invention provide isomer preparations having less than 100 ppm volatile organic compounds, and preferably less than 5 ppm volatile organic compounds.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: M (molar); mM (millimolar); $\mu$M (micromolar); kg (kilograms); g (grams); mg (milligrams); $\mu$g (micrograms); ng (nanograms); L or l (liters); ml (milliliters); $\mu$l (microliters); cm (centimeters); mm (millimeters); nm (nanometers); ° C. (degrees centigrade); KOH (potassium hydroxide); HCL (hydrochloric acid); and Hg (mercury).

EXAMPLE 1

Preparation of CLA Isomers

This Example describes the production c11,t13 octadecadienoic acid from t10,c12 octadecadienoic acid. Fifty grams of KOH were dissolved in propylene glycol under moderate heating. One hundred grams of 98% linoleic acid were then added to the mixture, and the mixture heated to 150° C. and stirred for 3 hours. The mixture was then cooled and washed several times with hot water and then dried under vacuum at moderate heat. The resulting CLA mixture consisted of c9,t11 and t10,c12 octadecadienoic acid as well as traces of CLA isomers. The mixture was converted to methylester by reflux boiling in acidic methanol. Fifty grams of conjugated free fatty acids were dissolved in methanol containing 4.5% sulfuric acid and boiled under reflux conditions for 1 hour in a water bath. The mixture was cooled and the bottom layer discarded. Fresh methanol with 4.5% sulfuric acid was added and the mixture boiled for an additional hour under reflux conditions. After cooling, this methylester mixture was washed several times with water and then dried under vacuum at moderate heat. Ten grams of the methylester were dissolved in acetone and cooled overnight to −60° C. in a freezer. A solid precipitate was recovered by filtration and re-dissolved in acetone and again cooled to −60° C. overnight. The precipitate was dried under vacuum and shown by GLC analysis to contain 97% t10,c12 CLA. The analytical equipment consisted of a Perkin Elmer GLC with autosampler. The column was a highly polar fused silica type. The following program setting were used:

| Injection: | Splitless at 250° C. |
| --- | --- |
| Detection: | Flame Ionization Detector at 280° C. |
| Carrier: | Helium at psig. |
| Oven program: | 80° C.–130° C. (45° C./min), then 1° C./min to 220° C. and 220° C. throughout for 10 min. |
| Column: | WCOT FUSED SILICA 0.25 mm × 100 m, CP-SIL 88 for FAME, df = 0.2. |

One gram of purified t10,c12 isomer was then covered with nitrogen in a sealed tube and heated for two hours at 220° C. After cooling, the resulting methylesters were analyzed by GC as above. The relative content of t10,c12 in the mixture was reduced to 52.32% and the c11,t13 isomer was present at a level of 41.96% (See Table 2).

TABLE 2

Conversion of t10,c12 isomer to c11,t13 isomer

| Isomer | % Before heating | % After heating |
| --- | --- | --- |
| c11,t13 | 0 | 41.57 |
| t10,c12 | 97.34 | 51.72 |
| C11,c13 | 0 | 1.44 |
| c10,c12 | 0 | 2.70 |
| t11,t13 | 0 | 0.54 |
| t10,t12 | 0.7 | 1.05 |

EXAMPLE 2

Preparation of CLA Isomers

This Example describes the production t8,c10 octadecadienoic acid from c9,t11 octadecadienoic acid. Purified c9,t11 octadecadienoic acid may be obtained from commercial sources (Matreya, State College, Pa.) or by fermentation with rumen microorganisms (See, e.g., U.S. Pat. No. 5,674,901, incorporated herein by reference). The purified c9,t11 octadecadienoic is converted to a high percentage (e.g., 25% to 50%) t8,c10 octadecadienoic acid by placing the c9,t11 octadecadienoic acid in a sealed tube under nitrogen and heating to 220° C. for about 2 hours.

EXAMPLE 3

Preparation of CLA Isomers

This Example describes the production t6,c8 octadecadienoic acid from c7,t9 octadecadienoic acid. Purified c7,t9 octadecadienoic acid may be obtained by preparative scale gas chromatography. The purified c7,t9 octadecadienoic is converted to a high percentage (e.g., 25% to 50%) t6,c8 octadecadienoic acid by placing the c9,t11 octadecadienoic acid in a sealed tube under nitrogen and heating to 220° C. for about 2 hours.

EXAMPLE 4

Preparation of CLA Isomers

This Example describes the production c12,t14 octadecadienoic acid from t11,c13 octadecadienoic acid. Purified t11,c13 octadecadienoic acid may be obtained by preparative scale gas chromatography (e.g., following the process described in Example 1). The purified t11,c13 octadecadienoic is converted to a high percentage (e.g., 25% to 50%) c12,t14 octadecadienoic acid by placing the c9,t11 octadecadienoic acid in a sealed tube under nitrogen and heating to 220° C. for about 2 hours.

EXAMPLE 5

Preparation of CLA Isomers

This Example describes the production t5,c6 octadecadienoic acid from c6,t8 octadecadienoic acid. Purified c6,t8 octadecadienoic acid may be obtained by preparative scale gas chromatography. The purified c6,t8 octadecadienoic is converted to a high percentage (e.g., 25% to 50%) t5,c6 octadecadienoic acid by placing the c9,t11 octadecadienoic acid in a sealed tube under nitrogen and heating to 220° C. for about 2 hours.

EXAMPLE 6

Preparation of CLA Isomers

This Example describes the production t4,c6 octadecadienoic acid from c5,t7 octadecadienoic acid. Purified c5,t7 octadecadienoic acid may be obtained by preparative scale gas chromatography. The purified c5,t7 octadecadienoic is converted to a high percentage (e.g., 25% to 50%) t4,c6 octadecadienoic acid by placing the c9,t11 octadecadienoic acid in a sealed tube under nitrogen and heating to 220° C. for about 2 hours.

EXAMPLE 7

Preparation of CLA Isomers

This Example describes the production t3,c5 octadecadienoic acid from c4,t6 octadecadienoic acid. Purified c4,t6 octadecadienoic acid may be obtained by preparative scale gas chromatography. The purified c4,t6 octadecadienoic is converted to a high percentage (e.g., 25% to 50%) t3,c5 octadecadienoic acid by placing the c9,t11 octadecadienoic acid in a sealed tube under nitrogen and heating to 220° C. for about 2 hours.

EXAMPLE 8

Preparation of CLA Isomers

This Example describes the production of c13,t15 octadecadienoic acid from t12,c14 octadecadienoic acid. Purified t12,c14 octadecadienoic acid may be obtained by preparative scale gas chromatography. The purified t12,c14 octadecadienoic is converted to a high percentage (e.g., 25% to 50%) c13,t15 octadecadienoic acid by placing the c9,t11 octadecadienoic acid in a sealed tube under nitrogen and heating to 220° C. for about 2 hours.

EXAMPLE 9

Preparation of CLA Isomers

This Example describes the production of c14,t16 octadecadienoic acid from t13,c15 octadecadienoic acid. Purified t13,c15 octadecadienoic acid may be obtained by preparative scale gas chromatography. The purified t13,c15 octadecadienoic is converted to a high percentage (e.g., 25% to 50%) c14,t16 octadecadienoic acid by placing the c9,t11 octadecadienoic acid in a sealed tube under nitrogen and heating to 220° C. for about 2 hours.

EXAMPLE 10

The Preparation of Triacylglycerols of CLA by Direct Esterification

Immobilized *Candida antarctica* lipase (1.25 g) is added to a mixture of glycerol (1.22 g, 13.3 mmol) and the desired CLA isomer. The mixture is gently stirred on a magnetic stirrer hot plate at 65° C. under continuous vacuum of 0.01–0.5 Torr. The volatile water produced during the progress of the reaction is continuously condensed into liquid nitrogen cooled traps. After 48 h the reaction is discontinued, n-hexane added and the enzyme separated off by filtration. The organic phase is treated with an alkaline aqueous solution of sodium carbonate to remove excessive free fatty acids (when required). The organic solvent (after drying over anhydrous magnesium sulfate when appropriate) is removed in vacuo on a rotary evaporator followed by high-vacuum treatment to produce the virtually pure product. When stoichiometric amounts of free fatty acids are used, titration by standardized sodium hydroxide is applied to determine the free fatty acid content of the crude reaction product.

EXAMPLE 11

Rations Containing CLA Isomers

This Example provides typical animal rations containing the CLA free fatty acids, triglycerides, and esters of the present invention. The CLA isomer preparation may be in the form of free fatty acids, alkylesters, triglycerides, or combinations thereof. It is not intended that the present invention be limited to any particular formulation. Indeed, it intended that CLA isomers in various concentrations will find use in a variety of rations.

A. PIG STARTER RATIONS

TABLE 3

| Ingredients | lbs. | kgs. |
|---|---|---|
| Corn, yellow (8.4% protein) | 1067 | 484.7 |
| Soy bean meal, solvent extracted, dehulled (47% protein) | 570 | 259 |
| CLA isomer prep. | 5 | 2.3 |
| Whey, dried (12.0% protein) | 300 | 136 |
| Dicalcium phosphate | 24 | 11 |
| Limestone | 16 | 7 |
| Iodized salt | 5 | 2 |

TABLE 3-continued

| Ingredients | lbs. | kgs. |
|---|---|---|
| Trace mineral premix | 5 | 2 |
| Vitamin premix | 8 | 4 |
| Totals | 2000 | 908 |

B. GROWER-FINISHER RATIONS FOR PIGS (FROM 40–240 LBS [18–109 KGS])

TABLE 4

| Ingredients | lbs. | kgs. |
|---|---|---|
| Corn, yellow (8.4% protein) | 1566 | |
| Soybean meal, solvent extracted (44% protein) | 380 | |
| CLA isomer prep. | 5 | |
| Dicalcium phosphate | 21 | |
| Limestone | 15 | |
| Iodized Salt | 5 | |
| Trace Mineral Premix | 3 | |
| Vitamin Premix | 3 | |
| Total | 2000 | |

C. PIG GROWER FINISHER RATIONS (FOR PIGS 121–240 LBS [55–109 KGS])

TABLE 5

| Ingredients | lbs. | kgs. |
|---|---|---|
| Corn, yellow (8.4% protein) | 1687 | |
| Soybean meal, solvent extracted (44% protein) | 265 | |
| CLA isomer prep. | 5 | |
| Dicalcium phosphate | 18 | |
| Limestone | 15 | |
| Iodized salt | 5 | |
| Trace mineral premix | 2 | |
| Vitamin premix | 3 | |
| Total | 2000 | |

1. COMPOSITION AND ANALYSIS OF PIG TRACE MINERAL REMIX

TABLE 6

| Element | Source | Amount (lbs) |
|---|---|---|
| Copper (Co) | Copper Sulfate | 1.500 |
| Iodine (I) | Potassium Iodide | 0.010 |
| Iron (Fe) | Ferrous Sulfate | 25.000 |
| Manganese (Mn) | Manganese Sulfate | 2.500 |
| Selenium (Se) | Sodium Selemite) | 0.025 |
| Zinc (Zn) | Zinc Sulfate | 25.000 |
| | Carrier | 45.965 |
| Total | | 100.000 |

2. COMPOSITION OF PIG VITAMIN PREMIX

TABLE 7

| Vitamins | Amount |
|---|---|
| Essential | |
| Vitamin A (million IU) | 5.0 |
| Vitamin D (million IU) | 0.6 |

TABLE 7-continued

| Vitamins | Amount |
|---|---|
| Vitamin E (thousand IU) | 26.0 |
| Niacin (g) | 25.0 |
| d-Pantothenic acid (g) | 20.0 |
| Riboflavin (g) | 6.0 |
| Vitamin B-12 (mg) | 25.0 |
| Optional | |
| Biotin (g) | 0.3 |
| Menadione (g) | 4.0 |
| Carrier | to 10 lbs |
| Total | 10.0 |

D. 18% PROTEIN LAYER RATIONS FOR HENS

TABLE 8

| Ingredients | lbs. | kgs. |
|---|---|---|
| Ground yellow corn | 1242 | 564.5 |
| CLA isomer prep. | 5 | 2.3 |
| Alfalfa meal, 17% | 25 | 11.3 |
| Soybean meal, dehulled | 451.6 | 205.3 |
| Meat and bone meal (47%) | 50 | 23.0 |
| DL-methionine | 1.0 | .5 |
| Dicalcium phosphate | 7 | 3.1 |
| Ground limestone | 174 | 79.1 |
| Iodized salt | 7 | 3.1 |
| Stabilized yellow grease | 37 | 17.2 |
| Mineral and vitamin supplements | | |
| Calcium pantothenate (mg) | 5,000 | |
| Manganese (g) | 52 | |
| Selenium (mg) | 90.8 | |
| Zinc (g) | 16 | |
| Vitamin A (IU) | 6,000,000 | |
| Vitamin $D_3$ (IU) | 2,000,000 | |
| Choline (mg) | 274,000 | |
| Niacin (mg) | 12,000 | |
| Riboflavin (mg) | 2,000 | |
| Vitamin B-12 | 6 | |
| Total | 2000 | 909.4 |

E. STARTER AND FINISHER RATIONS FOR BROILERS

TABLE 9

| | Starter (up to 24 days) | | Finisher (25 days to market) | |
|---|---|---|---|---|
| Ingredients | lbs | kgs. | lbs. | kgs. |
| Ground yellow corn | 1,106 | 503 | 1235 | 561 |
| CLA isomer prep. | 5 | 2.3 | 5 | 2.3 |
| Soybean meal, dehulled | 605 | 275 | 420 | 191 |
| Alfalfa meal, 17% | — | — | 25 | 11 |
| Corn gluten meal, 60% | 50 | 23 | 75 | 34 |
| Fish meal, herring, 65% | 50 | 23 | 50 | 23 |
| Meat and bone meal, 47% | 50 | 23 | 50 | 23 |
| Dicalcium phosphate | 10 | 4 | 9 | 4 |
| Ground limestone | 16 | 7 | 14 | 6.3 |
| DL-methionine | 0.8 | 0.3 | — | — |
| Stabilized yellow grease | 101 | 45.7 | 110 | 49.4 |
| Iodized salt | 7 | 3 | 7 | 3 |
| Mineral and vitamin supplement | | | | |
| Calcium pantothenate (mg) | 5,000 | | 5,000 | |
| Manganese (g) | 75 | | 75 | |
| Organic arsenical supplement | 0.1 | | 0.1 | |
| Selenium (mg) | 90.8 | | 90.8 | |
| Zinc (g) | 30 | | 30 | |
| Vitamin A (IU) | 4,000,000 | | 4,000,000 | |
| Vitamin D (IU) | 1,000,000 | | 1,000,000 | |
| Vitamin E (mg) | 2,000 | | 2,000 | |
| Vitamin K (mg) | 2,000 | | 2,000 | |
| Choline (mg) | 503,000 | | 672,000 | |
| Niacin (mg) | 20,000 | | 20,000 | |
| Riboflavin (mg) | 3,000 | | 3,000 | |
| Vitamin B-12 (mg) | 12 | | 12 | |
| Total | 2000.9 | 909.3 | 2000.1 | 909.5 |

F. GROWER/FINISHER TURKEY RATIONS

TABLE 10

| | Grower (8–16 weeks) | | Finisher (16 weeks–market) | |
|---|---|---|---|---|
| Ingredients | lbs. | kgs. | lbs. | kgs. |
| Ground yellow corn | 1194 | 595 | 1490 | 677.2 |
| Wheat middlings | 50 | 23 | — | — |
| Alfalfa meal, 17% | 25 | 11.3 | 25 | 11.3 |
| Soybean meal, dehulled | 570 | 259 | 335 | 152.3 |
| Meat and bone meal, 47% | 50 | 23 | 50 | 23 |
| Dicalcium phosphate | 32 | 14.5 | 23 | 10.5 |
| Ground limestone | 14 | 6 | 17 | 8 |
| Stabilized yellow grease | 45 | 20.7 | 45 | 20.7 |
| CLA isomer prep. | 5 | 2.3 | 5 | 2.3 |
| Iodized Salt | 10 | 4.5 | 10 | 4.5 |
| Mineral and vitamin supplements | | | | |
| Calcium pantothenate (mg) | 4,500 | | 4,500 | |
| Manganese (g) | 30 | | 30 | |
| Selenium (mg) | 181.6 | | 181.6 | |
| Zinc (g) | 30 | | 30 | |
| Vitamin (IU) | 1,500,000 | | 7,500,000 | |
| Vitamin D (IU) | 1,700,000 | | 1,700,000 | |
| Vitaniin E (IU) | 10,000 | | 10,000 | |
| Biotin (mg) | 100 | | 100 | |
| Choline (mg) | 388,000 | | 417,000 | |
| Niacin (mg) | 46,000 | | 48,000 | |
| Riboflavin (mg) | 5,000 | | 5,000 | |
| Vitamin B-12 | 6 | | 6 | |
| Total | 2000 | 909.3 | 2000 | 909.3 |

G. DRY DOG FOOD FORMULA

TABLE 11

| Ingredients | Formula 1, % | Formula 2, % |
|---|---|---|
| Meat and bone meal, 50% CP | 8.0 | 15.0 |
| Fish meal, 60% CP, low fat | 5.0 | 3.0 |
| Soybean meal, 44% CP | 12.0 | — |
| Soybean meal, 50% CP | — | 19.0 |
| Wheat germ meal, 25% CP | 8.0 | 5.0 |
| Skimmed milk, dried | 4.0 | 2.75 |
| Cereal grains, mixed | 51.23 | — |
| Corn, flaked | — | 23.25 |
| Wheat bran | 4.0 | — |
| Wheat, flaked | — | 23.35 |
| Animal fat | 1.75 | 2.75 |
| CLA isomer prep. | .25 | .25 |
| Steamed bone meal | 2.0 | — |
| Brewers yeast | 2.0 | 5.0 |
| Fermentation solubles, dehydrated | 1.0 | — |

TABLE 11-continued

| Ingredients | Formula 1, % | Formula 2, % |
|---|---|---|
| Salt and trace minerals | 0.5 | 0.5 |
| Vitamin mixture | 0.25 | 0.25 |
| Ferric oxide | 0.02 | — |
| Total | 100.00 | 100.00 |

H. SEMI-MOIST DOG FOOD FORMULA

TABLE 12

| Ingredients | Formula 1, % | Formula 2, % |
|---|---|---|
| Soy flakes | 30.9 | 33.5 |
| Meat byproducts, 70% moisture | 32.0 | — |
| Meat and bone meal, dehydrated | — | 7.3 |
| Water | — | 25.6 |
| Sugar | 21.0 | 21.0 |
| Calcium and phosphorous supplement | 3.3 | — |
| Soybean hulls | 3.1 | 3.1 |
| Skimmed milk, dried | 2.5 | — |
| Propylene glycol | 2.1 | 2.1 |
| Sorbitol | 2.0 | 2.0 |
| Animal fat | .75 | 3.95 |
| CLA isomer prep. | .25 | .25 |
| Emulsifiers | 0.9 | — |
| Potassium sorbate | 0.35 | 0.35 |
| Salt | 0.6 | 0.6 |
| Vitamins | 0.25 | 0.25 |
| Total | 100.000 | 100.000 |

EXAMPLE 12

Production of Triacylglycerides

CLA isomers are prepared as described above and distilled on a molecular distillation plant at 150° C. and a pressure of $10^{-2}$ mbar. Next, 1000 kg of the distilled product is mixed with 97 kg of pure glycerol and 80 kg lipase. The reaction is allowed to proceed for 12 hours at 55° C. under vacuum and with stirring. The triacylglyceride product is distilled on a molecular distillation apparatus to remove unreacted fatty acids.

It is clear from above that the present invention provides methods for preparing novel compositions of CLA isomers. These CLA isomers may be used for various purposes, including but not limited to, gas chromatography controls and for controls in feeding studies, as well as nutritional supplements for humans and animals.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in food science, animal science, medicine, biochemistry, or related fields are intended to be within the scope of the following claims.

What is claimed is:

1. A method comprising:
   a) providing a first partially purified octadecadienoic isomer having a conjugated bond system; and
   b) treating said partially purified octadecadienoic isomer under conditions such that said conjugated bond system migrates, thereby forming a mixture comprising at least said first partially purified octadecadienoic acid isomer and a second octadecadienoic acid isomer.

2. The method of claim 1, further comprising step
   c) separating said first partially purified octadecadienoic acid isomer and said second octadecadienoic acid isomer to provide a second partially purified octadecadienoic acid isomer.

3. The method of claim 1, wherein said conditions comprise heating said partially purified octadecadienoic acid isomer.

4. The method of claim 2, wherein said separating step is accomplished by gas liquid chromatography.

5. The method of claim 1, wherein said octadecadienoic acid isomer comprises an alkylester.

6. The method of claim 1, wherein said first partially purified octadecadienoic acid isomer is one of c9,t11 and t8,c10 octadecadienoic acids and said second octadecadienoic acid isomer is the other of t8,c10 and c9,t11 octadecadienoic acids.

7. The method of claim 1, wherein said first partially purified octadecadienoic acid isomer is one of t10,c12 and c11,t13 octadecadienoic acids and said second octadecadienoic acid isomer is the other of t10,c12 and c11,t13 octadecadienoic acids.

8. The method of claim 1, wherein said first partially purified octadecadienoic acid isomer is one of c7,t9 and t6,c8 octadecadienoic acids and said second octadecadienoic isomer the other of c7,t9 and t6,c8 octadecadienoic acids.

9. The method of claim 1, wherein said first partially purified octadecadienoic acid isomer is one of t11,c13 and c12,t14 octadecadienoic acids and said second octadecadienoic acid isomer is the other of t11,c13 and c12,t14 octadecadienoic acids.

10. The method of claim 1, wherein said first partially purified octadecadienoic isomer is one of c6,t8 and t5,c6 octadecadienoic acids and said second octadecadienoic isomer is the other of c6,t8 and t5,c6 octadecadienoic acids.

11. The method of claim 1, wherein said first partially purified octadecadienoic acid isomer is one of c5,t7 and t4,c6 octadecadienoic acids and said second octadecadienoic isomer is the other of c5,t7 and t4,c6 octadecadienoic acids.

12. The method of claim 1, wherein said first partially purified octadecadienoic acid isomer is one of t3,c5 and c4,t6 octadecadienoic acids and said second octadecadienoic acid isomer is the other of c4,t6 and t3,c5 octadecadienoic acids.

13. The method of claim 1, wherein said first partially purified octadecadienoic acid isomer is one of t12,c14 and c13,t15 octadecadienoic acids and said second octadecadienoic acid isomer is the other of t12,c14 and c13,t15 octadecadienoic acids.

14. The method of claim 1, wherein said first partially purified octadecadienoic acid isomer is one of c14,t16 and t13,c15 octadecadienoic acids and said second octadecadienoic acid isomer is the other of said c14,t16 and t13,c15 octadecadienoic acids.

15. The composition produced by the method of claim 1.

16. The composition of claim 14, wherein said second isomer is present in a concentration greater than 30% of said first partially purified isomer.

17. The composition of claim 14, wherein said second isomer is present in a concentration greater than 40% of said first partially purified isomer.

18. The composition of claim 14, wherein said second isomer is present in a concentration between 20% and 80% of said first partially purified isomer.

19. A method comprising:
a) providing a first partially purified octadecadienoic isomer having a conjugated bond system;
b) treating said first partially purified octadecadienoic isomer under conditions such that said conjugated bond system migrates, thereby forming a mixture comprising said first partially purified octadecadienoic acid isomer and a second octadecadienoic acid isomer; and
c) separating said first partially purified octadecadienoic acid isomer and said second octadecadienoic acid isomer to provide a second partially purified octadecadienoic acid isomer.

20. The method of claim 19, wherein said conditions comprise heating said substantially purified octadecadienoic acid isomer.

21. The method of claim 19, wherein said separating step is accomplished by gas liquid chromatography.

22. A composition comprising isomers of conjugated linoleic acid, wherein said composition comprises at least 25% of a first isomer of octadecadienoic acid and at least 25%, of a sister isomer of said first isomer.

23. The composition of claim 22, wherein said conjugated linoleic acid is or comprises an alkylester.

24. The composition of claim 22, wherein said conjugated linoleic acid is or comprises a triglyceride.

25. The composition of claim 22, wherein said first isomer is c9,t11 octadecadienoic acid and said sister isomer is t8,c10 octadecadienoic acid.

26. The composition of claim 22, wherein said first isomer is t10,c12 octadecadienoic acid and said sister isomer is c11,t13 octadecadienoic acid.

27. The composition of claim 22, wherein said first isomer is c7,t9 octadecadienoic acid and said sister isomer is t6,c8 octadecadienoic acid.

28. The composition of claim 22, wherein said first isomer is t11,c13 octadecadienoic acid and said sister isomer is c12,t14 octadecadienoic acid.

29. The composition of claim 22, wherein said first isomer is c6,t8 octadecadienoic acid and said sister isomer is t5,c6 octadecadienoic acid.

30. The composition of claim 22, wherein said first isomer is c5,t7 octadecadienoic acid and said sister isomer is t4,c6 octadecadienoic acid.

31. The composition of claim 22, wherein said first isomer is c4,t6 octadecadienoic acid and said sister isomer is t3,c5 octadecadienoic acid.

32. The composition of claim 22, wherein said first isomer is t12,c14 octadecadienoic acid and said sister isomer is c13,t15 octadecadienoic acid.

33. The composition of claim 22, wherein said first isomer is t13,c15 octadecadienoic acid and said sister isomer is c14,t16 octadecadienoic acid.

* * * * *